United States Patent [19]
Lin et al.

[11] Patent Number: 5,591,139
[45] Date of Patent: Jan. 7, 1997

[54] IC-PROCESSED MICRONEEDLES

[75] Inventors: Liwei Lin; Albert P. Pisano, both of Berkeley, Calif.

[73] Assignee: The Regents of the University of California, Oakland, Calif.

[21] Appl. No.: 254,328

[22] Filed: Jun. 6, 1994

[51] Int. Cl.⁶ ........................................ A61M 5/32
[52] U.S. Cl. ........................................ 604/264
[58] Field of Search ............................ 604/22, 264, 280, 604/30, 43, 51–53

[56]          References Cited
           U.S. PATENT DOCUMENTS

| | | |
|---|---|---|
| 4,221,567 | 9/1980 | Clark et al. . |
| 4,461,304 | 7/1984 | Kuperstein . |
| 4,478,222 | 10/1984 | Koning et al. . |
| 4,502,938 | 3/1985 | Covington et al. . |
| 4,874,499 | 10/1989 | Smith et al. ........................ 204/403 |
| 4,902,278 | 2/1990 | Maget et al. . |
| 4,969,468 | 11/1990 | Byers et al. . |
| 5,106,365 | 4/1992 | Hernandez . |
| 5,130,276 | 7/1992 | Adams et al. . |
| 5,285,131 | 2/1994 | Muller et al. . |

OTHER PUBLICATIONS

K. Najafi et al., "A High–Yield IC–Compatible Multichannel Recording Array," *IEEE Micro Trans. on Electron Devices*, vol. ED–32, pp. 1206–1211, Jul. 1985.

E. Bassous, "Fabrication of Novel Three–Dimensional Microstructures by the Anisotropic Etching of (100) and (110) Silicon," *IEEE Trans. on Electron Devices*, vol. Ed–25, No. 10, Oct. 1978.

L. Lin et al., "Bubble Forming on a Micro Line Heater", *Proceedings of ASME Winter Annual Meeting, Micromechanical Sensors, Actuators and Systems*, DSC–vol. 32, pp. 147–163, 1991.

R. M. Moroney et al., "Microtransport Induced by Ultrasonic Lamb Waves," *Applied Physics letters*, pp. 774–776, V59, Aug., 1991.

H. T. G. Van Lintel et al., "A Piezoelectric Micropump Based on Micromachining of Silicon," *Sensors and Actuators*, vol. 15, pp. 153–157, 1988.

M. Esashi et al., "Normally Closed Microvalve and Micropump Fabricated on a Silicon Wafer," *Sensors and Actuators*, vol. 20, pp. 163–169, Nov. 1989.

S. F. Bart et al., "Microfabricated Electrohydrodynamic Pumps," *Sensors and Actuators*, vol. 21, N1–3, pp. 193–197, Feb. 1990.

C. J. Kim et al., "Silicon–Processed Overhanging Microgripper," *IEEE/ASME Journal of Microelectromechanical Systems*, vol. 1, pp. 31–36, Mar. 1992.

L. Lin et al., "Microbubble Powered Actuators," *IEEE International Conference on Solid–State Sensors and Actuators, Transducers '91*, pp. 1041–1044, San Francisco, Jun. 1991.

L. Lin et al., "Vapor Bubble Formation on a Micro Heater in Confined and Unconfined Micro Channels," *ASME 1993 National Heat Transfer Conference*, Atlanta, Aug. 1993.

C. H. Mastrangelo et al., "Electrical and Optical Characteristics of Vacuum Sealed Polysilicon Microlamps," *IEEE Micro Trans. on Electron Devices*, vol. 39, pp. 1363–1375, Jun., 1992.

L. Lin et al., "Vacuum Encapsulated Lateral Microresonators," *Technical Digest, 7th Int. Conf. on Solid–State Sensors and Actuators* (270–273), Inst. of Electr. Eng. of Japan, 7–10 Jun. 1993, Yokohama, Japan.

K. Takahashi et al., "Integration of Multi–Microelectrode and Interface Circuits by Silicon Planar and Three–Dimensional Fabrication Technology," *Sensors and Actuators*, vol. 5, pp. 89–99, 1984.

K. Najafi et al., "Strength Characterization of Silicon Microprobes in Neurophysiological Tissues," *IEEE Trans. on Biomedical Engineering*, vol. 37, No. 5, pp. 474–481, May, 1990.

*Primary Examiner*—Manuel Mendez
*Attorney, Agent, or Firm*—Fish & Richardson P.C.

[57]          ABSTRACT

An IC-processed microneedle including an interface region and shaft. A shell defines an enclosed channel to form the shaft. The shaft has ports to permit fluid movement therethrough. Microheaters, microdetectors and additional devices may also be fabricated on the microneedle.

26 Claims, 14 Drawing Sheets

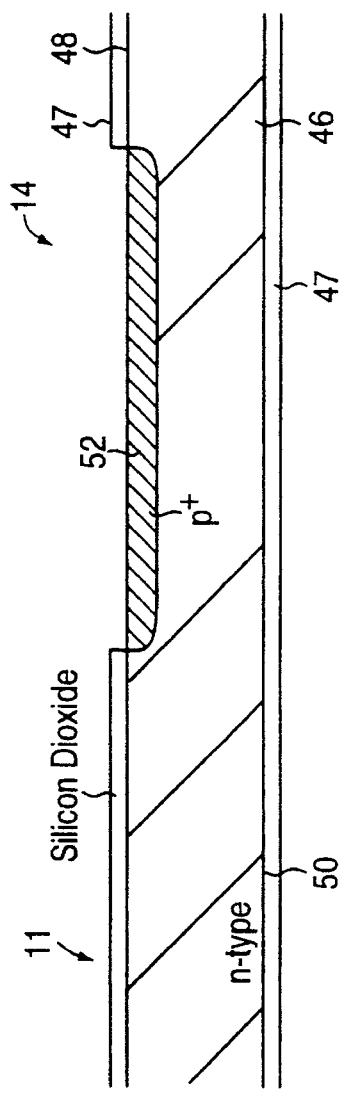
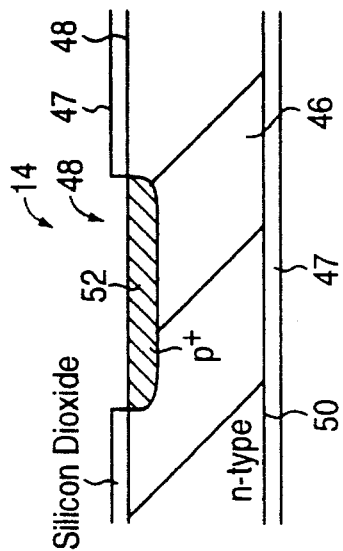
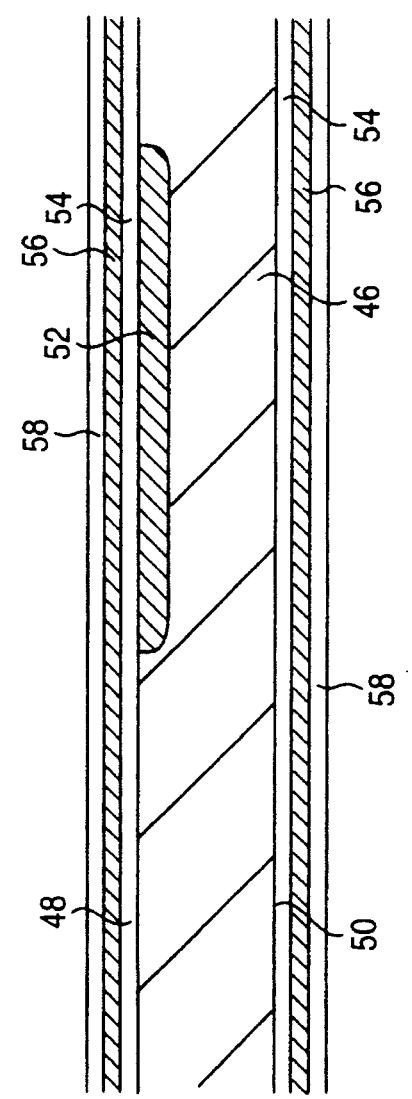
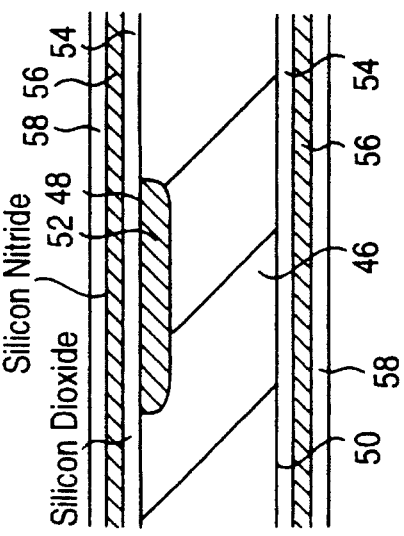
FIG. 3A-2
FIG. 3B-2
FIG. 3A-1
FIG. 3B-1

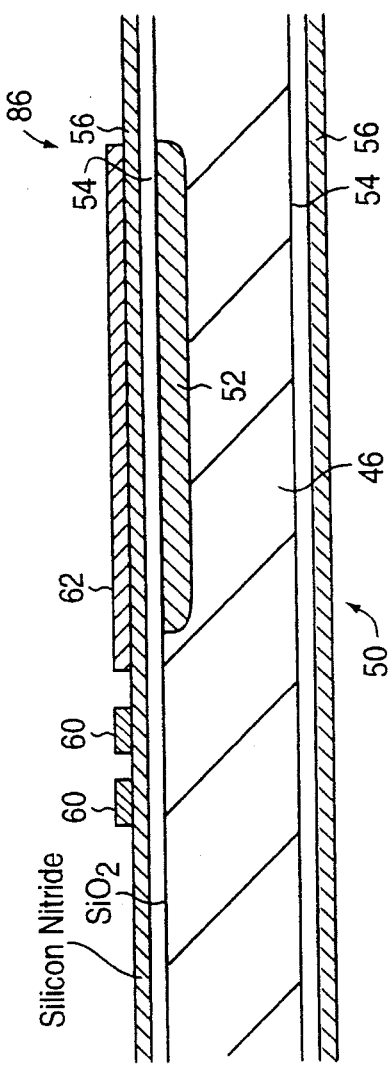
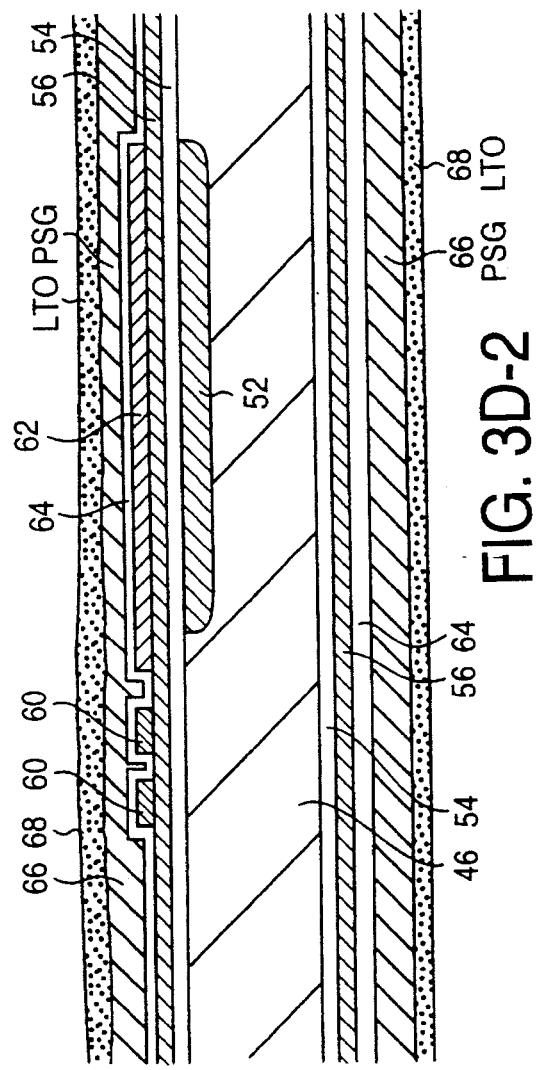
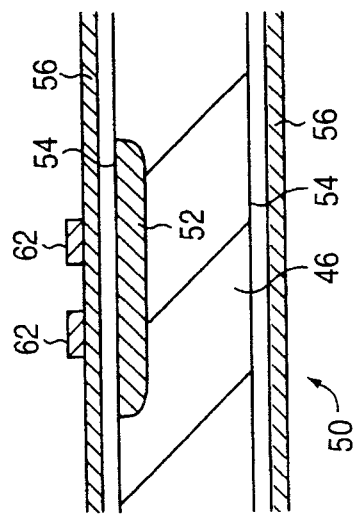
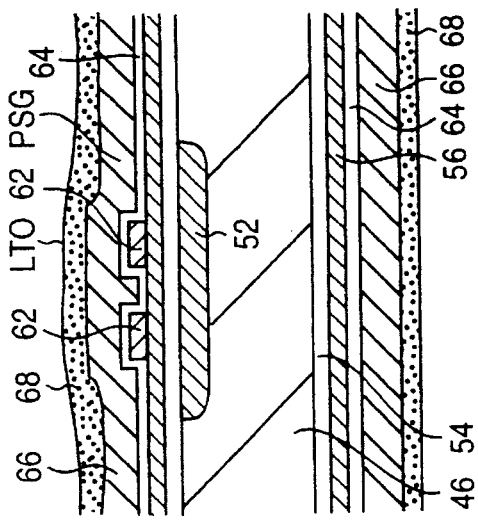

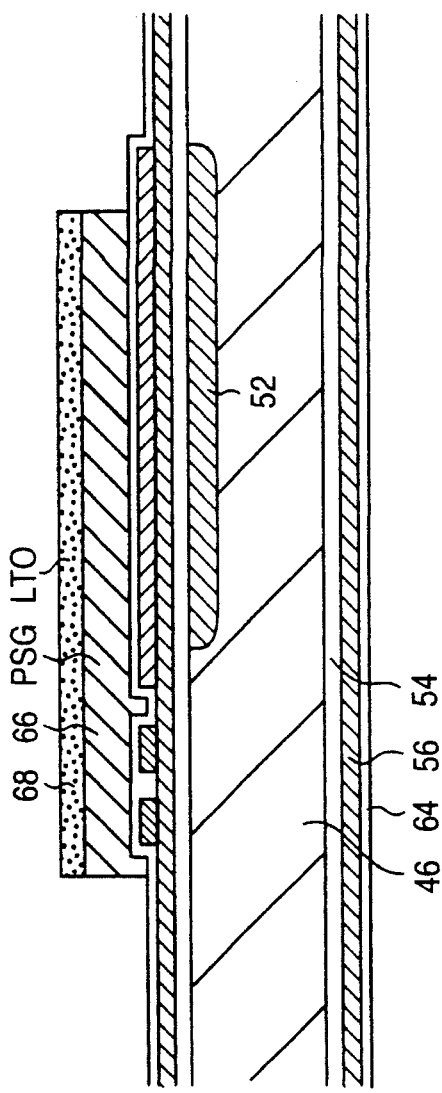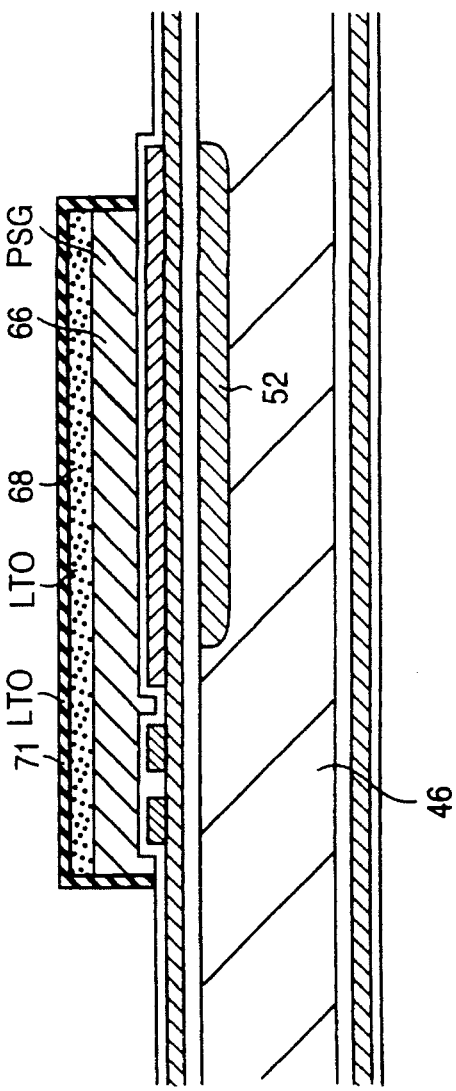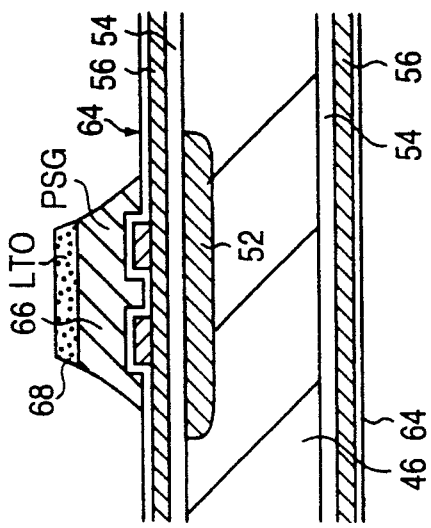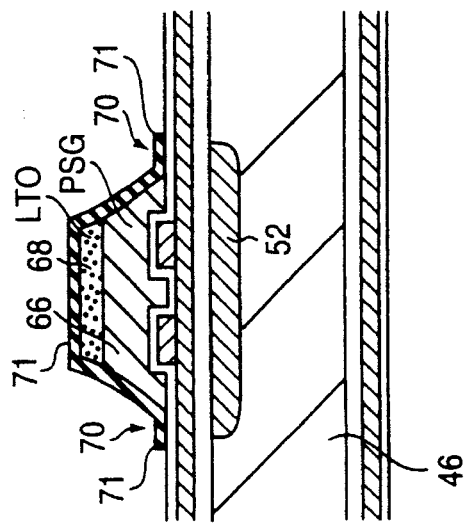

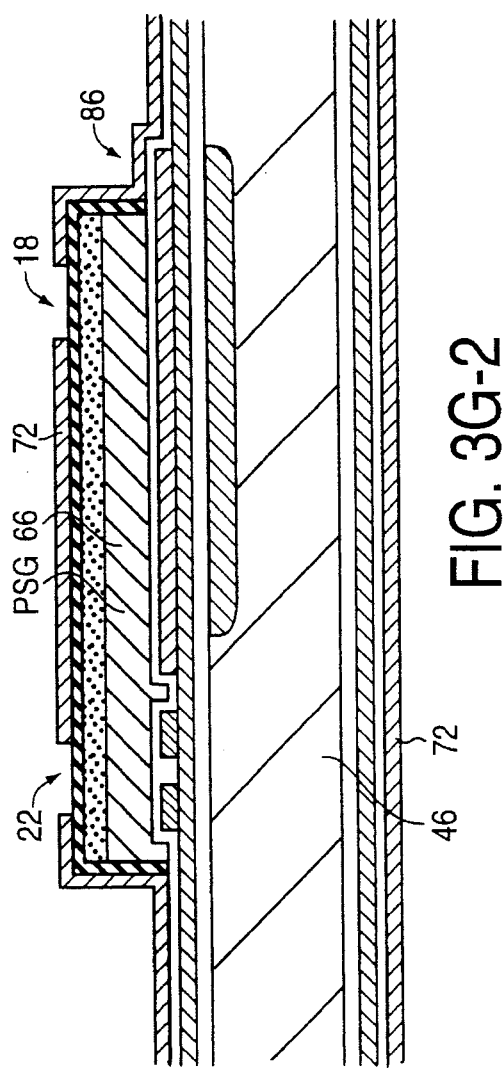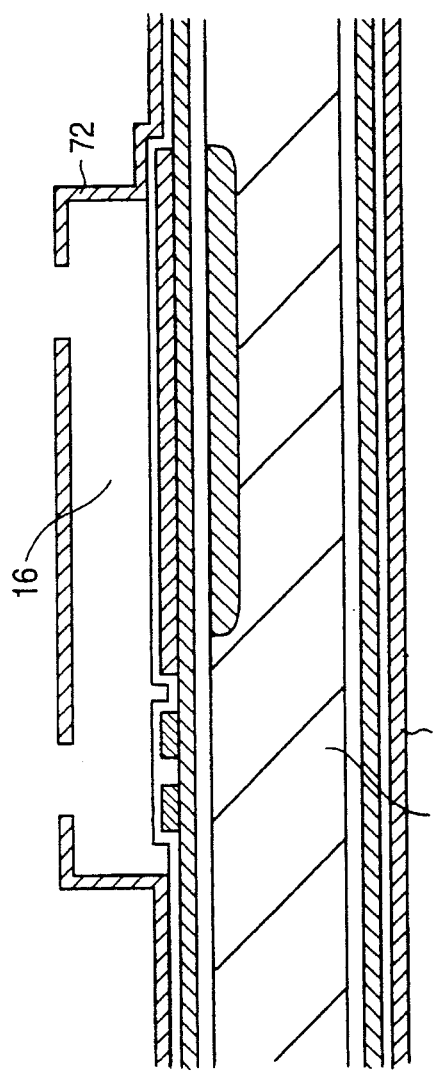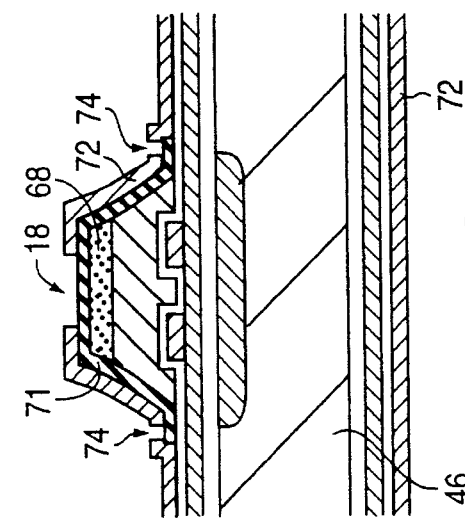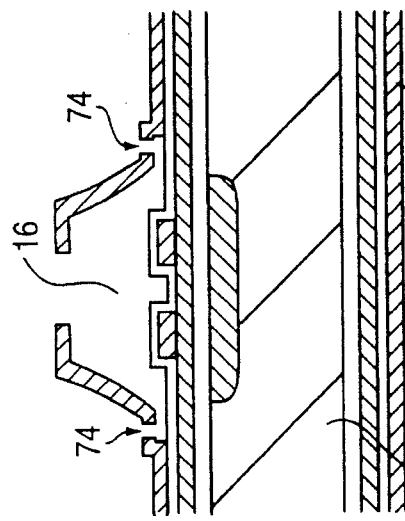

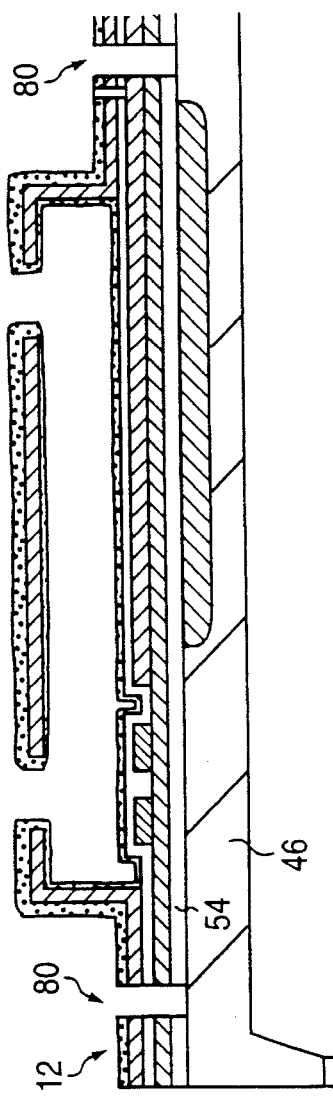
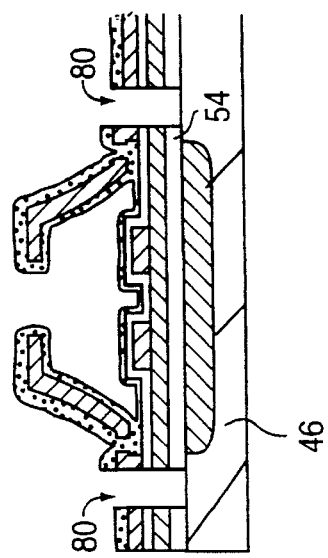
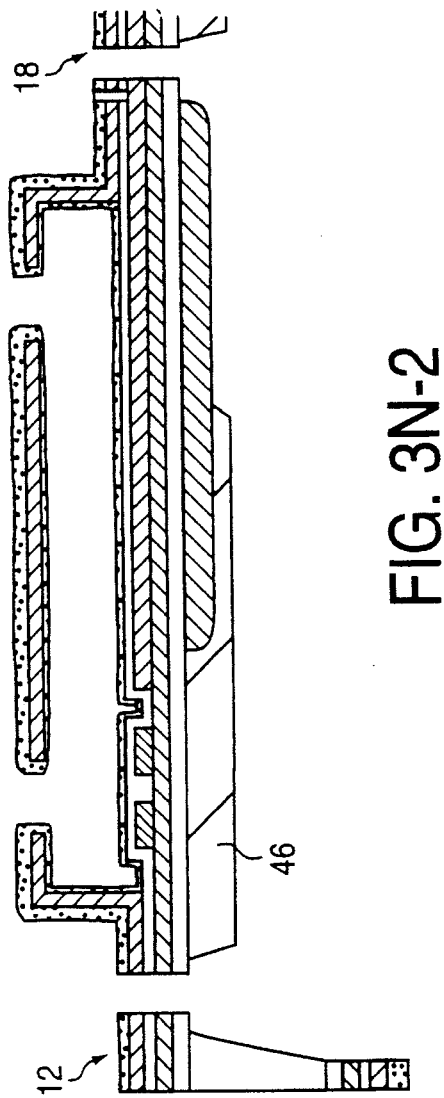
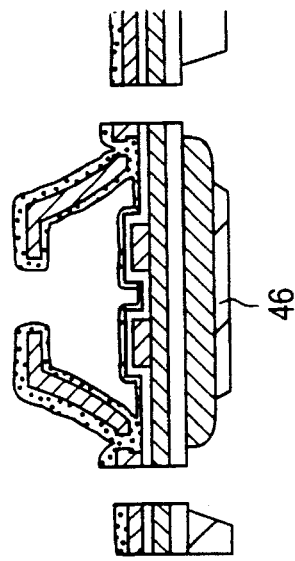
FIG. 3M-1
FIG. 3M-2
FIG. 3N-1
FIG. 3N-2

IC-PROCESSED MICRONEEDLES

This invention was made with Government support under Grant (Contract) No. EEC-8614900 awarded by the National Science Foundation. The Government has certain rights to this invention.

BACKGROUND OF THE INVENTION

The present invention relates generally to microneedles, and more particularly to microneedles fabricated by micromachining techniques.

As is well known, needles are used to extract samples of substances from living tissue in order to analyze the substances for diagnostic purposes, or to deliver a drug or a medicine. The majority of needles in use today are macroneedles, which have a relatively large diameter as compared to a blood cell and are on the order of millimeters (mm). The large diameter of the macroneedle shaft has the disadvantage of possibly damaging biological tissue during penetration. Additionally, tissue penetration by the needle is often painful to the patient because of the relatively large needle diameter.

One type of spring-actuated macroneedle penetrates tissue and drops blood to a chemical detector for measurement. While this needle may be less painful to the patient because penetration is of a relatively short duration, the needle is still relatively large and may damage tissue. Additionally, neither of the above-mentioned macroneedles provide real-time blood analysis.

As an alternative to macroneedles, microneedles having a diameter on the order of micrometers have many applications. For instance, they may be used as precise injection/extraction needles in cell biology, as injection/extraction heads in a drug delivery system or microchemical factory, and as injection/extraction heads in microsurgery. It is also advantageous to have a smaller size needle because the reduced size decreases discomfort and pain to the patient. This has been demonstrated in research on electrical microprobes made of silicon for an IC-compatible multichannel neural-recording array. The research has demonstrated that silicon microprobes with cross-sections on the order of tens of micrometers can penetrate living tissue without causing significant trauma. (K. Najafi, K. D. Wise and T. Mochizuki, "A High-Yield IC-Compatible Multichannel Recording Array," *IEEE Micro Trans. on Electron Devices*, vol. ED-32, pp. 1206–1211, July 1985.)

Recently, microneedles have been used with an inner diameter of approximately 20 micrometers (μm) (1 μm=1 micron=$10^{-6}$m). These microneedles are formed by heating the end of a glass pipette and lengthening the end until the diameter is reduced to about 20 μm. Most cells in an animal such as a human measure 10–20 micrometers in diameter. Thus, while these glass microneedles can be used to insert and withdraw fluids and gases from a single cell, it is difficult to control the size of the needle shaft during fabrication. Additionally, the resulting needle is not very strong and real-time blood analysis is not possible. Another disadvantage of glass pipette needles is that it is difficult to incorporate electronics with such needles.

In view of the foregoing, an object of the present invention is to provide a microneedle having controllable and relatively small dimensions, including shaft width, and a method for making the same.

Another object of the present invention is to provide a microneedle which permits real-time analysis of a fluid being sampled.

Yet another object of the present invention is to provide a microneedle which minimizes the amount of trauma to the tissue being penetrated.

Still another object of the present invention is to provide a microneedle which may be mass produced.

Yet still another object of the present invention is to provide a microneedle which is strong enough to reliably penetrate biological tissue.

A further object of the present invention is to provide a microneedle which may incorporate micropumps, microvalves and microdetectors.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to an IC-processed microneedle formed from a substrate which defines an interface region and an elongated portion extending away from the interface region. A shaft is formed from the elongated region by a shell, which defines an enclosed channel within the shaft. One end of the shaft is attached to the interface region. The shaft includes ports which permit fluid to flow through the microneedle.

The method of the present invention includes a sequence of steps for forming an IC-processed microneedle. First, a substrate is provided for forming an interface region and an elongated portion extending away from the interface region. A patterned non-planar etchable structure is then formed on the frontside of the elongated portion of the substrate. An unetchable membrane layer is deposited atop the etchable structure, and etching holes are opened in the membrane layer. One of the etching holes is at an end of the membrane layer and a second etching hole is positioned at a second end of the membrane layer. Next, the etchable structure is etched to a predetermined extent to form a cavity underneath the membrane layer, thereby producing a shaft formed from the membrane layer and the elongated portion of said substrate.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

DESCRIPTION OF THE PREFERRED EMBODIMENT

Figure 1A:
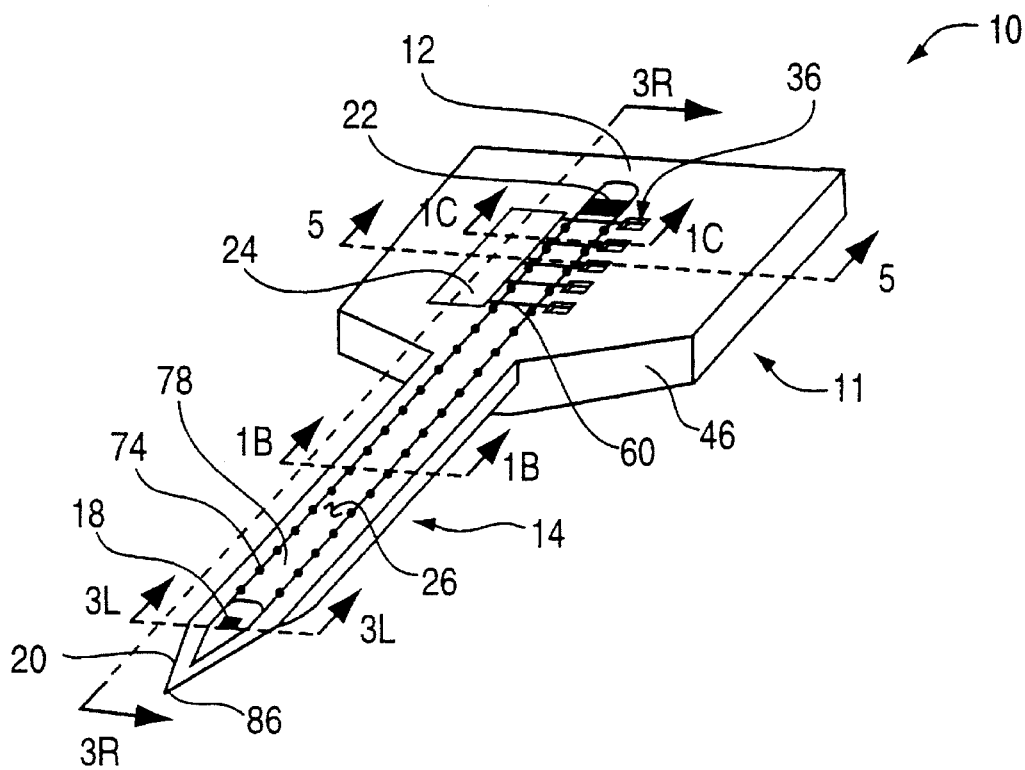
FIG. 1A is a perspective view of an embodiment of a silicon processed microneedle.

The present invention will be described in terms of the preferred embodiment. The preferred embodiment is an apparatus and method for fabricating IC-processed microneedles. Referring in detail to the drawings, wherein like reference numerals designate like parts in several figures, and initially to FIG. 1A, a microneedle in accordance with the present invention is illustrated.

Microneedle 10 includes an interface region 11 and a shaft 14 having a microflow channel 78 therein along its length. A distal end 20 of shaft 14 can be inserted into tissue (not shown) so that liquids (including gases) may be delivered to or taken from a patient, for example, via a distal fluid port 18. A shank fluid port 22 is located on shank or proximal end 12 of shaft 14 to deliver or receive fluids. The microneedle may include more than two ports, as desired. Microflow channel 78 runs along the length of fully-enclosed microneedle shaft 14. A series of thin polysilicon heating resistors 60 are located on interface region 11 along the floor of microflow channel 78. Interface region 11 is sufficiently thick to permit incorporation of on-chip electronics 24 for real-time fluid analysis. Heating resistors 60 may be used to form a thermally-driven, cascaded-bubble micropump or simple heater. The microneedle may also include detector resistors 62 which extend along the bottom of the microchannel (see FIG. 1B) and are coupled to electrodes 84 (FIG. 3L-2) on the tip 86 of the needle. Microflow channel 78 is formed by removing sacrificial layers from underneath a shell 26 during processing. In order to access the sacrificial layer, etch access holes 74 are opened and then filled after etching. The fabrication procedures will be discussed below in relation to FIGS. 3A-1 through 3N-2.

Figure 1B:
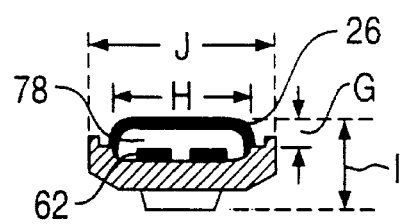
FIG. 1B is a cross-sectional view of the microneedle as taken along line 1B—1B of FIG. 1A.

FIG. 1B shows a cross-section of fully-enclosed microflow channel 78. The channel height is approximately 9 μm and is indicated by dimension "G" and the channel width "H" may be between 30 μm to 60 μm. The needle height "I" is about 70 82 m, and the needle width "J" is approximately 80 μm at the tip region.

Figure 1C:
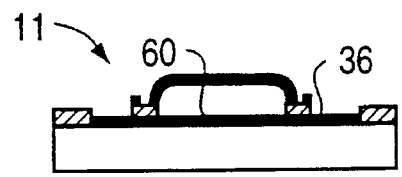
FIG. 1C is a cross-sectional view of the microneedle as taken along line 1C—1C of FIG. 1A.

FIG. 1C illustrates the positioning of a polysilicon resistor 60 on interface region 11. Contact pads 36 are situated on both sides of the microflow channel 78 at shank end 12 and provide an outside connection to resistors 60, which function as microheaters. Note that detector resistors 62 cannot be seen in FIG. 1C because this cross-section is taken along line 1C—1C on the interface region. The detector resistors extend along the length of the channel but do not extend into the interface region any further than is necessary to couple them to electronics 24. The location of both resistors can be best seen in FIG. 3N-2.

Figure 2A:
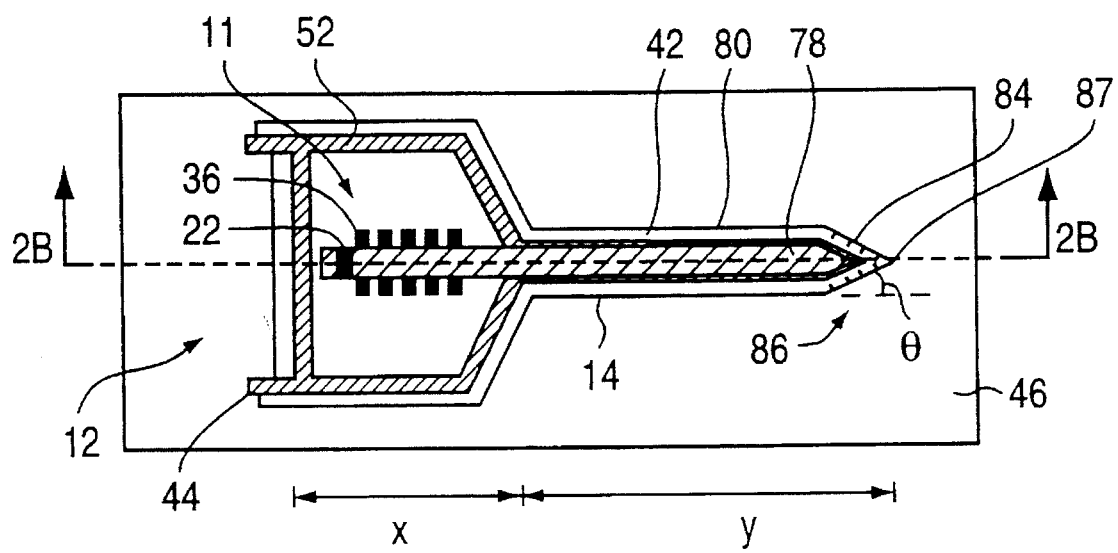
FIG. 2A is a plan view of the microneedle prior to detachment from the substrate.

FIG. 2A is a plan view of a microneedle 10 before it is separated from wafer or substrate 46 by breaking beams 44. Support beams 44 connect microneedle 10 to substrate 46 and facilitate testing and manipulation of the microneedle prior to its final use. Although only a single microneedle 10 is shown, many microneedles may be fabricated on a single wafer. Area 40 marks the area where microneedle 10 will be separated from substrate or thin-film 46. Interface region 11 may be used as an integrated-circuit (IC) interface region of approximately 2 to 3 millimeters (mm)$^2$. The tip region 86 is formed at an angle θ of approximately 45° to the plane of the needle shaft 14, to form a sharp triangular tip 87. The width of the interface region, indicated by dimension "X", is approximately 1.5 mm, and the length of the shaft indicated by dimension "Y", is between 1 and 6 mm. At shank end 12, interface region 11 widens out to a large surface area, suitable for incorporation of additional integrated electronic and/or fluidic devices.

Figure 2B:
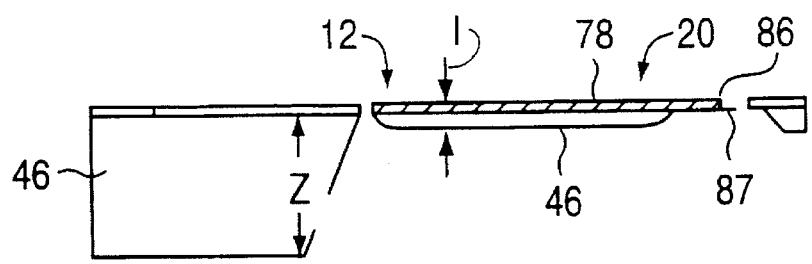
FIG. 2B is a cross-sectional view of the microneedle as taken along line 2B—2B of FIG. 2A.

Cross-sectional dimensions of a completed microneedle 10 are shown in FIG. 2B after if has been detached from wafer 46. Wafer 46 has an initial thickness of between 500 and 550 μm, as indicated by "Z". The wafer thickness of the microneedle is reduced during fabrication. Shaft 14 has a thickness of approximately 50 μm indicated by dimension "T". In microneedles which are 3 mm-long or longer, microneedle 10 tapers from the tip end 86, where it is approximately 80 μm wide, to 140 μm, where it joins the shank in order to increase strength. The retained single-crystal silicon layer 46 provides a rigid spine which adds strength to the needle. Note that there is no single-crystal silicon at the tip region 86, so that the tip is sharper and smaller than the portion of the shaft including single-crystal silicon.

The fabrication sequence for formation of a microneedle is shown in FIGS. 3A-1 to 3N-2. Seven masks may be used. The drawings are not to scale, and dimensions should be taken from the text; the drawings are to illustrate the process, and not necessarily the preferred dimensions of the microneedle. The microneedle is formed using IC (integrated circuit) processing methods, e.g. oxidation, lithography, chemical vapor deposition, doping, and etching. Briefly, microchannel 78 is surface-micromachined onto a single-crystal silicon substrate or thin-film 46 that is mostly etched from the wafer backside along shaft 14 in the final fabrication step. While only a single microneedle is shown in the following steps, it will be understood that many microneedles may be fabricated simultaneously on a single wafer.

Figure 1:
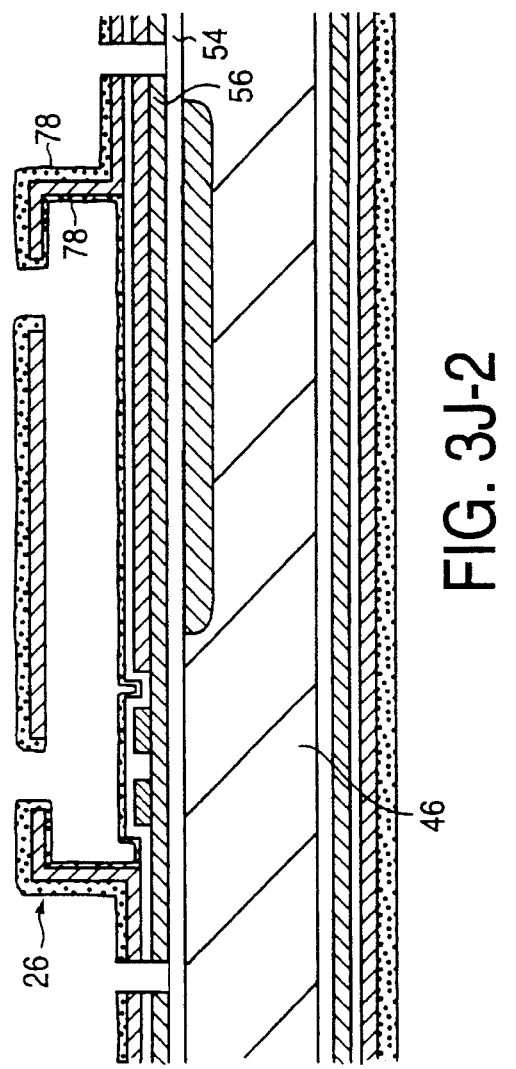
Figure 2:
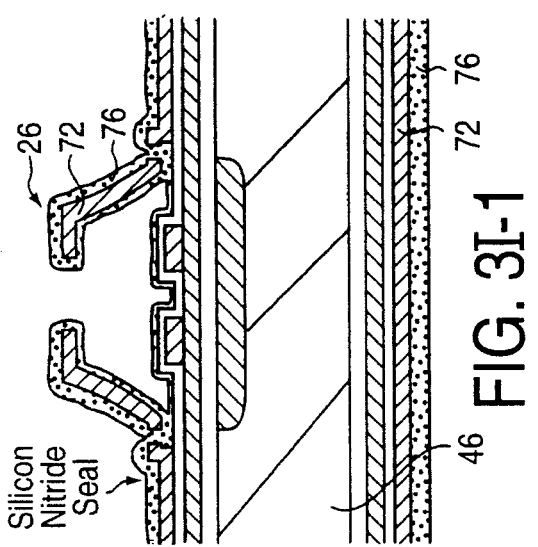

FIGS. 3A-1 AND 3A-2 show a <100>-oriented lightly doped n-type silicon wafer 46 which is 500–550 μm thick. A thick masking layer 47 of silicon dioxide ($SiO_2$) 1.2 μm thick is thermally grown on wafer frontside 48 and backside 50. Masking layer 47 is patterned as shown, and boron is diffused at approximately 1125° C. for fifteen hours to form a 12 μm-deep heavily doped p-type region 52. Both the future interface region 11 and shaft 14 are indicated generally in these figures. Boron-doped region 52 defines tip region 84 (FIG. 2A), extends along the needle shaft and defines the perimeter of interface region 11, as best shown in FIG. 2A. Boron-doped region 52 acts as an etchant stop since EDP (ethyleneidamine pyrocatacol and water), used during fabrication, does not etch boron-doped silicon. Note that the boron-doped region is omitted from the center of IC interface region 11 because, as well known, any electronic components incorporated into the microneedle must be atop undoped silicon.

Masking layer 47 is then removed, and a 400 nanometer (nm) thick layer 54 of $SiO_2$ is thermally grown on the wafer.

A 600 nm low-stress nitride layer 56 is then deposited by low pressure chemical vapor deposition (LPCVD) for passivation. As well known, CVD will deposit on all exposed surfaces of the wafer. Silicon dioxide layer 54 will serve as a thermal barrier underneath the microheater as well as an electronic insulation layer. Silicon nitride layer 56 serves as the bottom layer of the microchannel. Next, a 600 nm-thick LPCVD phosphorus-doped polycrystalline silicon layer 58 is then deposited, and the resulting structure is as shown in FIGS. 3B-1 and 3B-2.

Polysilicon layer 58 is patterned and etched to define polysilicon heating resistors 60 on interface region 11 (FIG. 3C-1) and, if desired, polysilicon detector resistors 62 (FIG. 3C-2). Note that phosphorus-doped polycrystalline silicon layer 58 is also etched away on backside 50. Resistors 60 are shown perpendicular to the length of channel 78; however, they may also be fabricated such that they extend lengthwise parallel to channel 78 or in any other orientation under the area of fluid flow. Resistors 60 are approximately 50 μm long. Detector resistors 62 extend lengthwise along shaft 14 and function as wires to relay a signal from electrodes or recording sites 84 (FIG. 2A) to the shank end of the channel, where electronics 24 process the signals. There is one resistor for each electrode and so the width of channel 78 determines the number of electrodes which may be fabricated within the channel. The microneedle shown has two resistors, but more electrodes could be incorporated into the microneedle by widening the channel or altering the aspect ratio of the resistors. Both heating resistors 60 and detector resistors 62 are approximately 0.5 μm high, and 2 μm wide. Heating resistors 60 are approximately 50 μm long. The length of detector resistors 62 depends upon the eventual length of shaft 14. However, resistors 62 should reach the tip of the needle so that electrodes or recording sites may also be at the needle tip 86.

Referring now to FIGS. 3D-1 and 3D-2, a thin layer 64 of approximately 150 nm of LPCVD low-stress nitride is deposited to cover and protect polysilicon resistors 60 and 62 during subsequent EDP (ethyleneidamine pyrocatacol and water) etching. A layer 66 of 5 μm phosphosilicate glass (PSG) is deposited by LPCVD process and then an approximately 3 μm layer 68 of a low-temperature oxide (LTO) such as undoped LPCVD SiO$_2$ is deposited. The LTO layer on top of the PSG gives better adhesion to photoresist. The LTO layer also desirably minimizes hydrofluoric acid (HF) attack on the interface between the photoresist and PSG. Furthermore, no high-temperature densification process is needed so that the future circuitry in the IC interface region 11 will not be damaged.

The microflow channel is then patterned and wet-etched in a 5:1 solution of buffered HF, as shown in FIGS. 3E-1 AND 3E-2. The buffered HF etches both PSG 66 and LTO 68 layers as shown. The primary configuration of the channel is formed by this etch. A 0.5 μm LTO layer 71 (FIGS. 3F-1 and 3F-2) is then deposited by LPCVD to provide an area for future etch access holes. The resulting shell formed from LTO layers 68 and 71 is approximately 3–4 μm. LTO layer 71 is then patterned and wet-etched in 5:1 BHF (buffered hydrofluoric acid) to provide an etch channels area 70 as shown in FIG. 3F-1. Dry-etching is also possible for this step. LTO layer 71 is also deposited on backside 50, but is not shown because they it is removed after the BHF wet-etch. The etch channels area 70 is advantageously only about 0.5 μm thick because it will be relatively easy to fill etch holes later in the fabrication process, as will become apparent below.

The wafer is then coated with a 1 μm thick layer 72 of LPCVD low-stress silicon nitride which will become a portion of the microchannel shell 26 (FIG. 1B). Etch access holes 74 and distal 18 and shank 22 fluid ports are defined and etched in a plasma etcher through silicon nitride layer 72. The etch access holes lead to the sacrificial PSG and LTO layers which will be etched. The cross-section appears as in FIG. 3G-1; the etch access holes are not visible in FIG. 3G-2. Etch access holes are formed along the length of the shaft 14 in etch channel area 70, and are located every 25 μm. The duration of the sacrificial-layer etching step is thus independent of channel length. The etch access holes are approximately 5 μm×5 μm.

Fluid ports 18 and 22 will permit flow of a liquid through the microchannel 78 when the needle is fully operational. The fluid ports are approximately 20 μm×20 μm. In a preferred embodiment, distal fluid port 18 is positioned 150 μm up the microneedle from the tip 86. Since the PSG and LTO layers are underneath nitride layer 72, resistors 60 and 62 will not be affected by this etch. Additionally, because the fluid ports are relatively large as compared to the etch access holes, the fluid ports will not be completely filled during deposition of silicon nitride sealing layer 76, in which etch access holes are sealed (described below). As an alternative, the fluid ports may be etched after the sacrificial PSG and LTO layers are removed from within the microchannel if good process control is employed. However, this method has the possible drawback of affecting silicon nitride 64, which protects resistors 60 and 62. Since layer 64 is approximately 150 nm, the resistors will not be affected because the etch will remove about 50 nm of layer 64. As another alternative, resistors 60 and 62 may be located so that they will not be underneath the fluid ports.

After the etch access holes and fluid ports have been formed, the wafer is immersed in concentrated hydrofluoric acid (48% HF) for approximately 2.5 minutes to remove PSG layer 66, and LTO layers 68 and 71 underneath nitride shell 72. Wafer 46 is then rinsed in de-ionized water, and any residual oxide is removed from the silicon nitride 72 using HF. The resulting microneedle is then as shown in FIGS. 3H-1 and 3H-2.

Figure 3I:
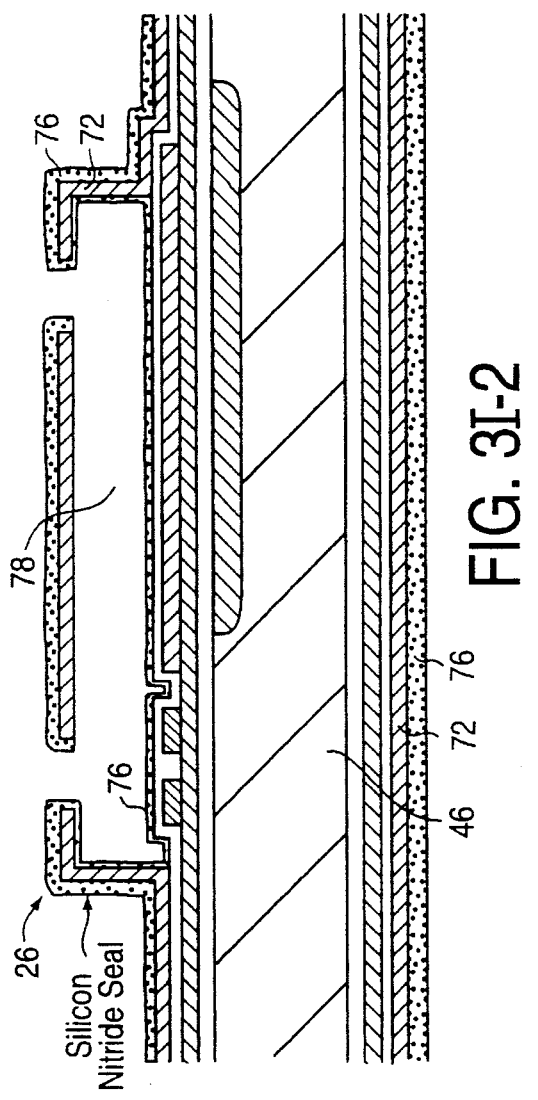
FIGS. 3A-1 to 3N-2 schematically illustrate a microneedle fabrication process according to the present invention. The left-hand figures are taken along line 3L—3L of FIG. 1A, and the right-hand figures are taken along line 3R—3R.

All etch access holes 74 are sealed by deposition of an additional 1.5 μm thick layer 76 of LPCVD low-stress nitride to form a shell 26, as shown in FIGS. 3I-1 and 3I-2. Since the thickness of the PSG before etching was only about 0.5 μm underneath the etch access holes 74, a 1.5 μm deposition of silicon nitride insures that the hole will be completely filled. Microchannel 78 is thus completely sealed, except for the fluid ports. Fluid ports 18 and 22 are sufficiently wide that they will not be sealed by deposition of the 1.5 μm silicon nitride sealing layer. The size of the fluid ports is somewhat reduced during this step, but they remain sufficiently large enough to permit adequate fluid flow. A thin layer 76 of silicon nitride is also deposited in channel 78, as shown.

It is possible to form channel 78 without including etch access holes 74 by using the fluid ports to remove the sacrificial PSG and LTO layers. However, this approach would require more time to fully evacuate the channel. A clear advantage would be that the previous sealing step could be omitted.

Figure 3J:
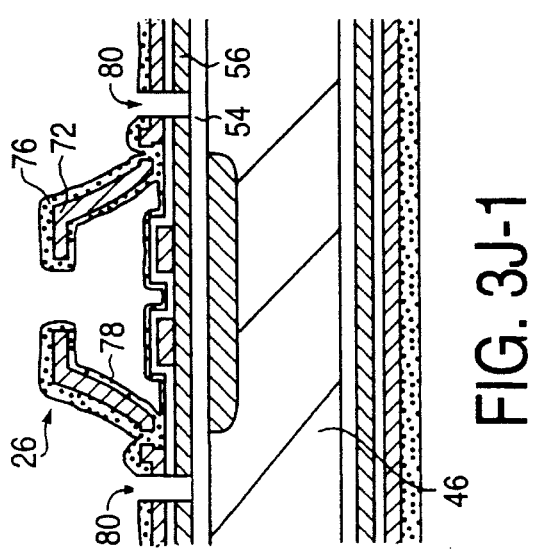

The needle has now been substantially fabricated, and steps to separate it from the wafer are now taken. EDP etch pre-openings or windows 80 are patterned by a mask and plasma etched in order to facilitate final separation of microneedle 10 from the rest of the wafer, as shown in FIGS. 3J-1 and 3J-2. Etch windows 80 are stopped at the 400 nm-thick SiO$_2$ layer 54. The etch windows will facilitate removal of the microneedle from the wafer during subsequent backside etch. It will be desirable later to remove both layers 54 and 56 in order to separate the microneedle. However, the etch is stopped at layer 54 at this point because it is relatively easy to etch silicon dioxide and relatively difficult to etch silicon nitride. Thus, silicon nitride layer 56 is removed from the frontside prior to backside etching.

Figures 2, 3K:
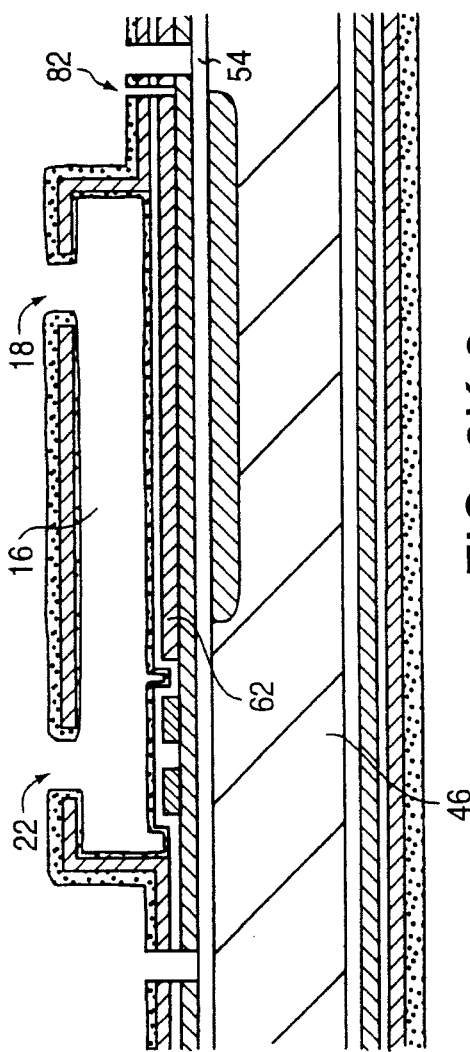
Figures 2, 3L:
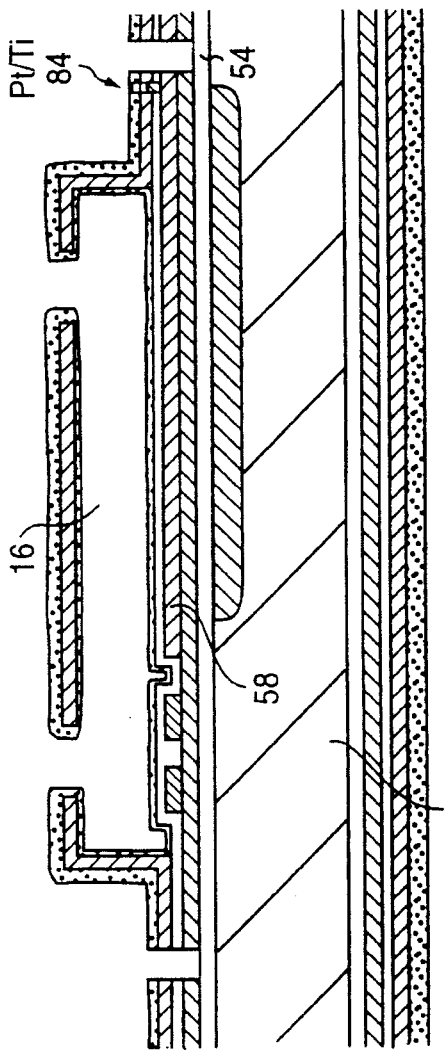
Figures 1, 3K:
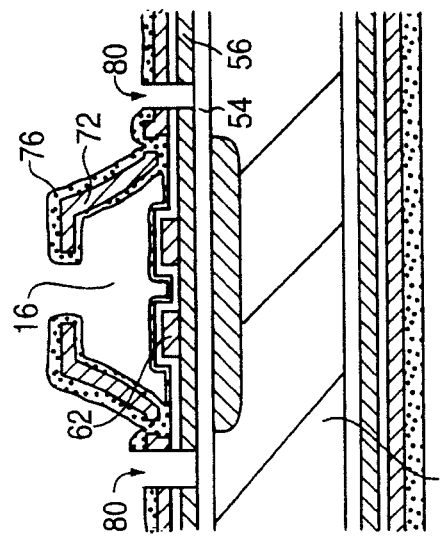
Figures 1, 3L:
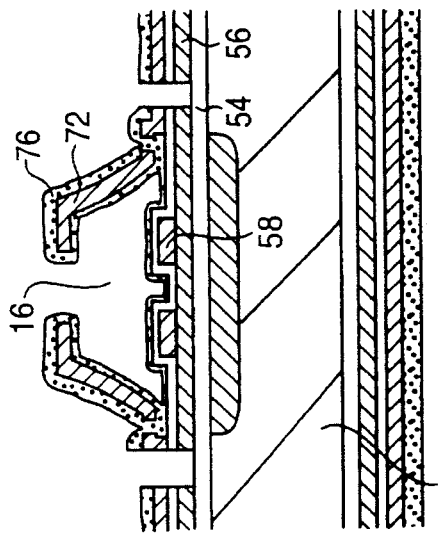

Next, an electrode hole 82 is formed by patterning and plasma-etching down to the 600 nm-thick phosphorus-doped polycrystalline silicon layer 58 to permit electrical contact with resistors 62. Only a single electrode hole 82 is shown in FIG. 3K-2 (the electrode is not visible in FIG. 3K-1), but the process for fabricating contact pads 36 (see FIG. 1C) is identical and is performed at the same time as electrode fabrication. The electrodes function as recording sites at distal end 20 and permit monitoring of biological electrical activity, as will be discussed below. The contact pads permit coupling of electronics with heating resistors 62. After electrode hole 82 is formed, a thin layer of titanium is deposited, followed by a thicker layer of platinum which completely fills the hole, forming a complete electrode 84 as shown in FIG. 3L-1. Again, the electrode is not visible in FIG. 3L-2.

At this point, microneedle 10 is essentially complete and must now be partially separated from wafer 46. The backside of the wafer is patterned with a blank mask and without alignment to open the etching areas of individual die to free the microneedles from the wafer backside. In a preferred fabrication method, the mask is positioned so that the microneedle tip extends to the blank center of the mask. Shank end 12 is covered by the mask and is not etched, but distal end 18 is not covered by the mask and so end 18 is completely etched. A timed EDP etch reduces the silicon wafer thickness to 120 µm, as shown in FIGS. 3M-1 and 3M-2. After rinsing in de-ionized water, the wafer is immersed in a 5:1 BHF solution which attacks only the pre-opened, bare $SiO_2$ layer 54. Pre-EDP etch window 80 is thus deepened so that it extends to undoped silicon layer 46.

Immersion in an EDP timed etch reduces the 120 µm thickness to 50 µm at shank end 12 as shown in FIGS. 3N-1 and 3N-2. As also shown in FIG. 2B, tip region 86 of shaft 14 does not contain any single-crystal silicon due to the corner-etching behavior of EDP. A combination of corner etching and etching from the crystal backside also removes the thicker non-doped single-crystal silicon for approximately 50 µm along the needle underside from the tip end. The corner etching behavior of EDP is addressed by B. Bassous in "Fabrication of Novel Three-Dimensional Microstructures by the Anisotropic Etching of (100) and (110) Silicon," *IEEE Trans. on Electron Devices*, Vol. Ed-25, No. 10, Oct. 1978.

The microneedle is then partially separated from the wafer, and remains attached through support beams 44, best shown in FIG. 2A. Since the many microneedles fabricated on wafer remain attached to the wafer, it is easier to package, transport, and handle the needles than if they were fully freed by the anisotropic etch. When a free-standing microneedle is desired, the microneedle is simply detached from the rest of the wafer by using, for example, tweezers or some other similar implement to apply pressure to beams 44. When the beams are broken, the microneedle is freed from the wafer.

Figure 4A:
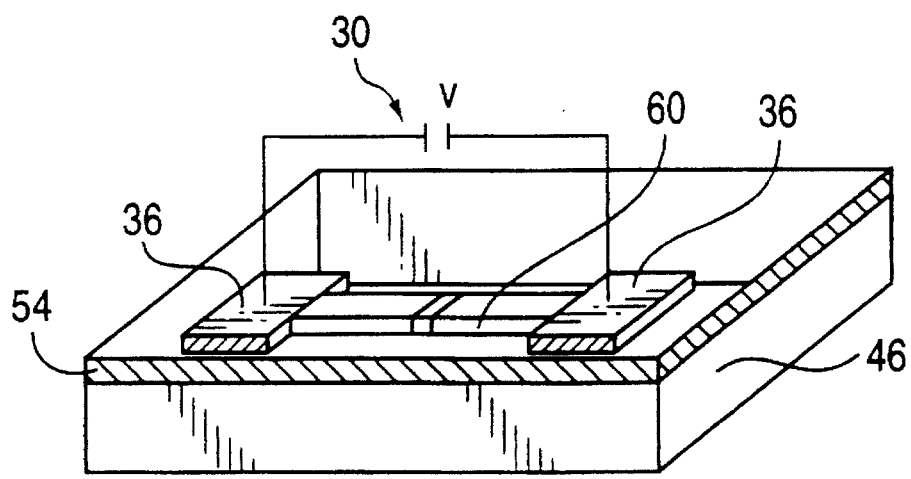
FIGS. 4A and 4B are views illustrating a microheater and its positioning relative to the microchannel, respectively.
Figure 4B:
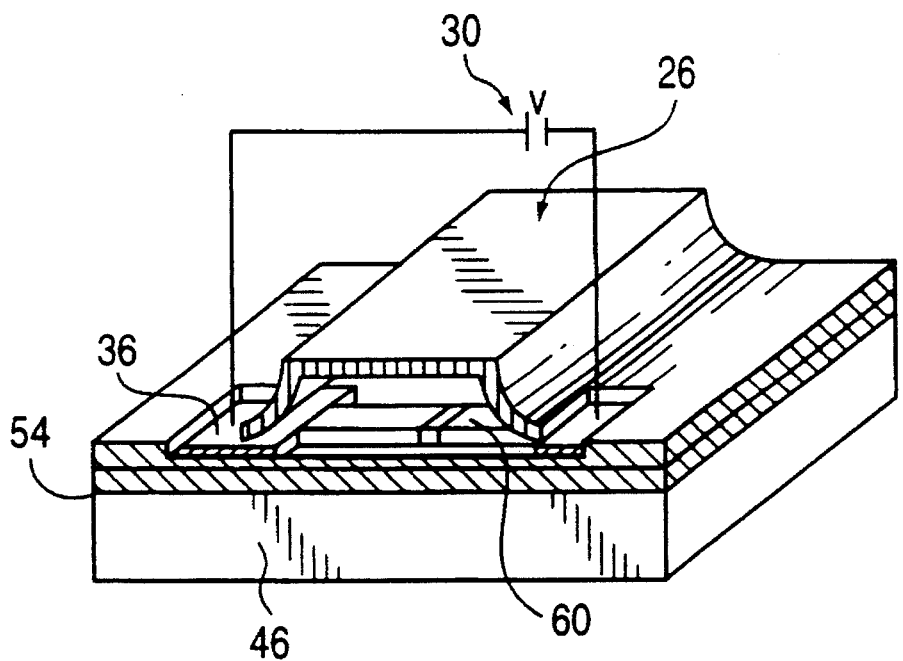

FIG. 4A shows a simplified view of resistor 60 and contact pads 36 (also FIG. 1C) of microneedle 10 (not shown). As explained above, the contact pads and resistor are defined on a single-doped polysilicon layer. A silicon dioxide layer 54 separates silicon substrate 46 and the contact pads and resistor. Resistor 60 functions as a microheater when a voltage source 30 supplies current to contact pads 36. The resistors propel a liquid to distal fluid port 18, as explained below. FIG. 4B illustrates the positioning of microneedle shell 26 above resistors 60. As noted above, since there is a silicon dioxide layer 54 underneath the polysilicon heater, heat conduction from the heater to silicon substrate 46 is restricted because $SiO_2$ layer 54 acts as an insulator. Due to the low power dissipated in the heater, the temperature of undoped silicon substrate 46 remains at the ambient temperature. The heaters are especially advantageous if a chemical reaction occurs quickly in response to heat. The reaction may occur in the microneedle and then may be quickly delivered to the appropriate tissue.

A single resistor is shown in FIGS. 4A and 4B to illustrate its positioning. However, in a preferred embodiment five resistors 60 form a thermally-driven cascaded bubble pump (FIG. 2A). In operation, the resistor furthest from the needle tip is heated and produces a single vapor bubble. Then, the adjacent resistor is heated and the bubble is moved sequentially down the line of resistors toward the distal end of the needle shaft. The resistors are heated quickly and sequentially, so that precise fluid control is possible. If a cascaded bubble pump is not employed, a fluid may move down the needle shaft simply by means of gravity.

In addition to resistors, micropumps and microvalves (neither is shown) may be incorporated onto the microneedle. For example, the resistors may also be part of a bubble-powered micropump coupled to an actuator. As discussed above, the bubble generation system creates individual, spherical vapor bubbles from 2 to 500 µm in diameter by locally heating a fluid with a thin film resistor. Prior research has shown that microbubbles are capable of actuating a polycrystalline silicon cantilever (See L. Lin and A. P. Pisano, "Bubble Forming on a Micro Line Heater", *Proceedings of ASME Winter Annual Meeting, Micromechanical Sensors, Actuators and Systems*, DSC-Vol. 32, pp. 147–163, 1991). Other micropumps can also be employed with these microneedles, such as those actuated by ultrasonic Lamb waves (See R. M. Moroney, R. M. White and R. T. Howe, "Microtransport Induced by Ultrasonic Lamb Waves," *Applied Physics letters*, pp. 774–776, V59, August, 1991); piezoelectrics (See H. T. G. Van Lintel, F. C. M. Van Deol and S. Bouwstra, "A Piezoelectric Micropump Based on Micromachining of Silicon," *Sensors and Actuators*, Vol. 15, pp. 153–157, 1988, and M. Esashi, S. Shoji and A. Nakano, "Normally Closed Microvalve and Micropump Fabricated on a Silicon Wafer," *Sensors and Actuators*, Vol. 20, pp. 163–169, November 1989); and electrohydrodynamics (See S. F. Bart, L. S. Tavrow, M. Mehregany and J. H. Lang, "Microfabricated Electrohydrodynamic Pumps," *Sensors and Actuators*, Vol. 21, 1–3, pp. 193–197, February 1990).

FIGS. 5A–5E briefly illustrate a process for fabricating a microneedle with on-chip CMOS (complementary metal-oxide semiconductor) devices. Both CMOS and BiCMOS are compatible with the microneedle fabrication process. The manufacturability of an on-chip electronic interface with the microneedle is essential for a broad range of applications. The manufacturabilities of the on-chip CMOS and bipolar CMOS devices with the IC-processed microneedle increase the signal conditioning ability, which is not a possible feature in needles fabricated by other means.

Figure 5A:
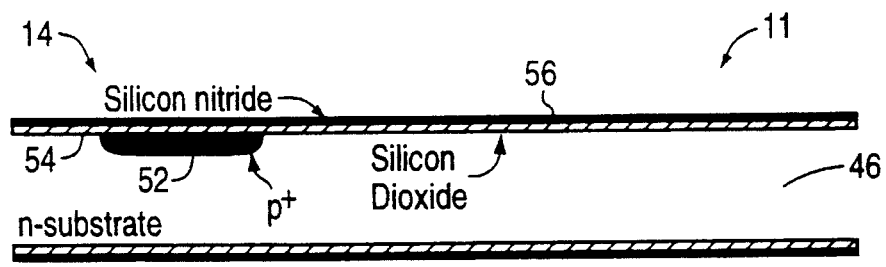
FIGS. 5A–5E show the sequence of steps in fabricating the microneedle with on-chip CMOS (complementary metal-oxide semiconductor) as taken along line 5—5 of FIG. 1A.
Figure 5B:
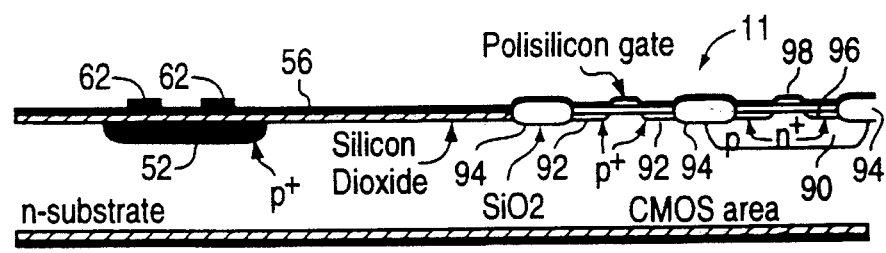

Formation of the microneedle itself is via the same steps illustrated in FIGS. 3A-1 to 3N-2, and the CMOS devices are fabricated using standard processes. FIGS. 5A–5E, illustrate the best mode sequence for integrating fabrication of both the microneedle and CMOS devices. FIGS. 5A–5E are taken along line 5—5 of FIG. 1A, although no CMOS devices are shown in FIG. 1A. FIG. 5A is a cross-sectional view of the partially constructed needle shaft 14 and the interface region 11. The heavily doped p-type region 52 has been formed and silicon dioxide 54 and silicon nitride 56 layers have been deposited on wafer 46, as explained in connection with FIG. 3B-1. Next, silicon dioxide 54 and silicon nitride 56 layers are removed from interface region 11, where the CMOS devices will be fabricated. CMOS fabrication then commences using standard processes, and a p-type well 90, p-type layer 92, thick $SiO_2$ layer 94, and n-type layer 96 are formed by known methods. Polysilicon layer 58 (see FIG. 3B-1) is then deposited and polysilicon gates 98 are defined with the same masking operation which defines polysilicon resistors 62 (see FIG. 3C-1). The resulting structure is as shown in FIG. 5B.

Figure 5C:
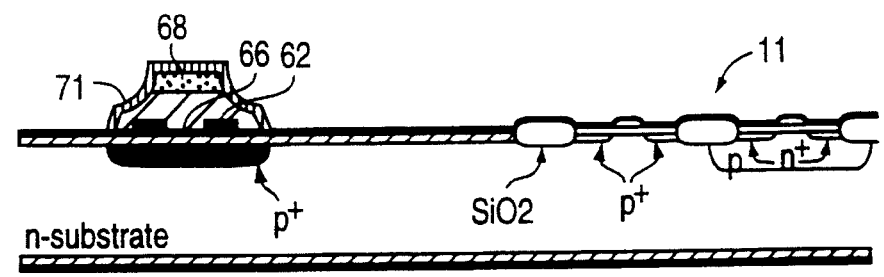
Figure 5D:
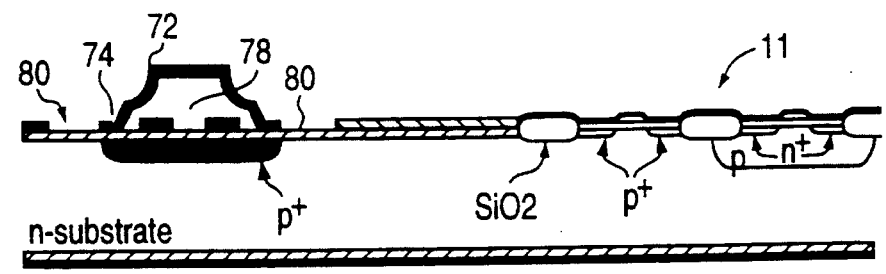

FIG. 5C shows PSG layer 66 and LTO layers 70 and 71, as in FIG. 3F-1. Etch access holes 74 are formed and the PSG and LTO layers are etched to form microchannel 78, as explained in conjunction with FIG. 3H-1. EDP etch preopenings or windows 80 are formed as explained in connection with FIG. 3J-1, and the resulting structure is shown in FIG. 5D. During these operations, interface region 11 is masked so that the CMOS devices will not be affected.

Figure 5E:
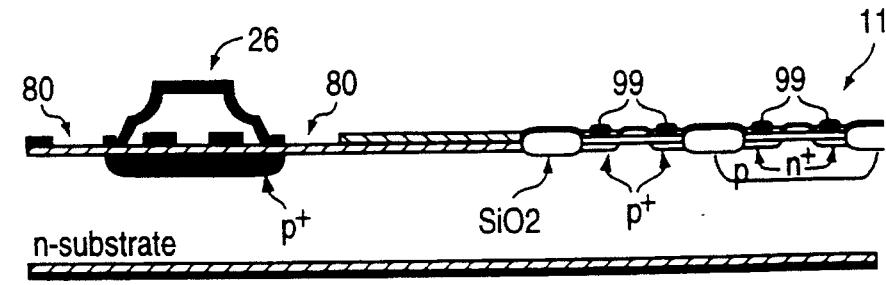

Next, CMOS device fabrication is completed when metal contacts 99 are formed which connect to p-type 92 and n-type 96 regions, as well known in the art. The resulting structure is as shown in FIG. 5E. The microneedle is then separated from the rest of the wafer, as explained in connection with FIGS. 3K-1 to 3L-2.

The microneedle of the present invention can be expected to have broad applications to fluid sampling, fluid delivery, and precisely located chemical-reaction stimulation. Microneedle 10 has successfully penetrated tissue without damage to the needle, due in part to the strong silicon backbone along the needle shaft. Since the microneedles have a thickness of approximately 70 μm (microchannel height, boron region plus single crystal region) over most of their length, they are relatively strong. Another advantage of the design of the microneedle is that during and after processing it is surrounded by regions of silicon having full wafer thickness, providing even greater strength, easy post processing and handling.

Figure 6:
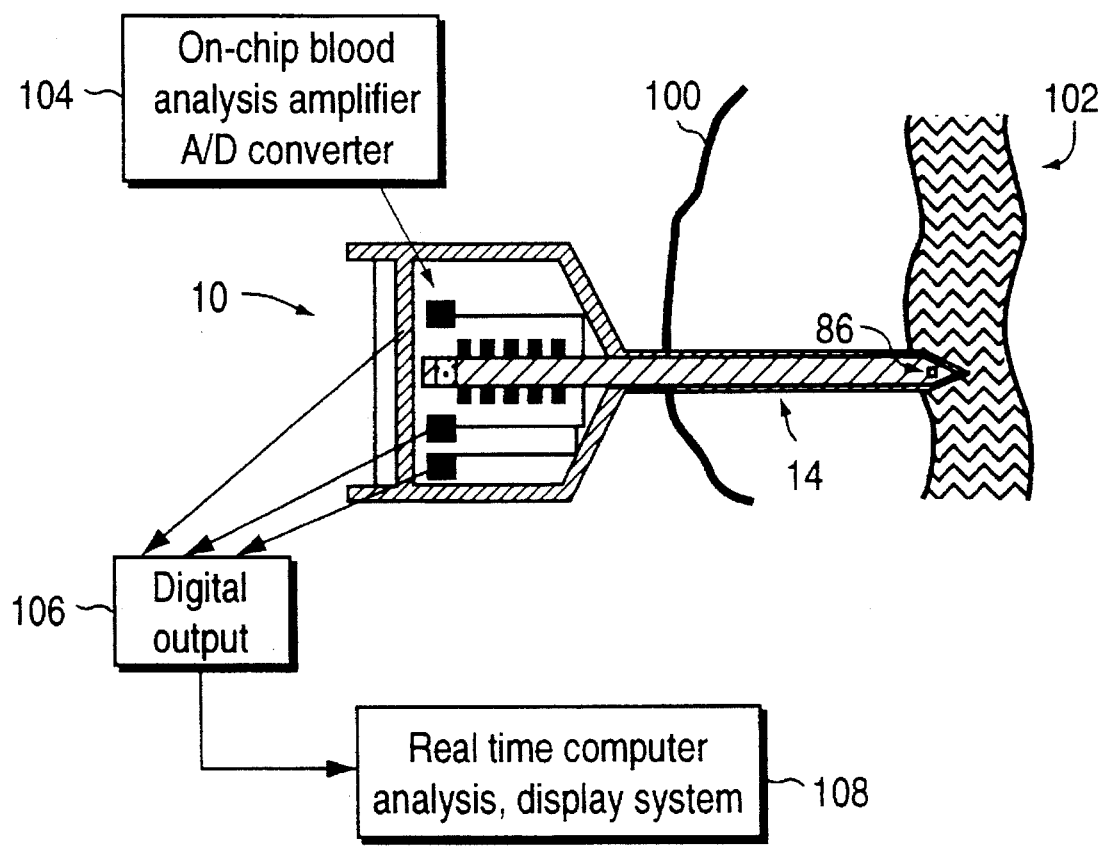
FIG. 6 is a schematic diagram showing the microneedle penetrating tissue in a first application of the present invention.

An application of the microneedle of the present invention is illustrated in FIG. 6, which shows a real-time blood analysis system. Tip 86 of microneedle 10 is inserted through tissue 100 into a blood vessel 102. As blood is drawn into the needle via shaft 14, the blood is analyzed by an on-chip blood analysis amplifier and A/D converter 104, which converts an analog signal to a digital signal for digital output 106. Digital output 106 is transmitted to a computer 108 for real-time computer analysis, and displayed, for example, on a cathode-ray tube. Since the diameter of shaft 14 is only approximately 50 μm, it causes minimal pain to the patient during penetration because there is little trauma to the tissue involved. Another possible application of the silicon-processed microneedle is administration of drugs on a long term basis. For instance, the microneedle may be implanted in a small tumor and used to administer small, concentrated doses of a drug on an extremely local level.

Figure 7:
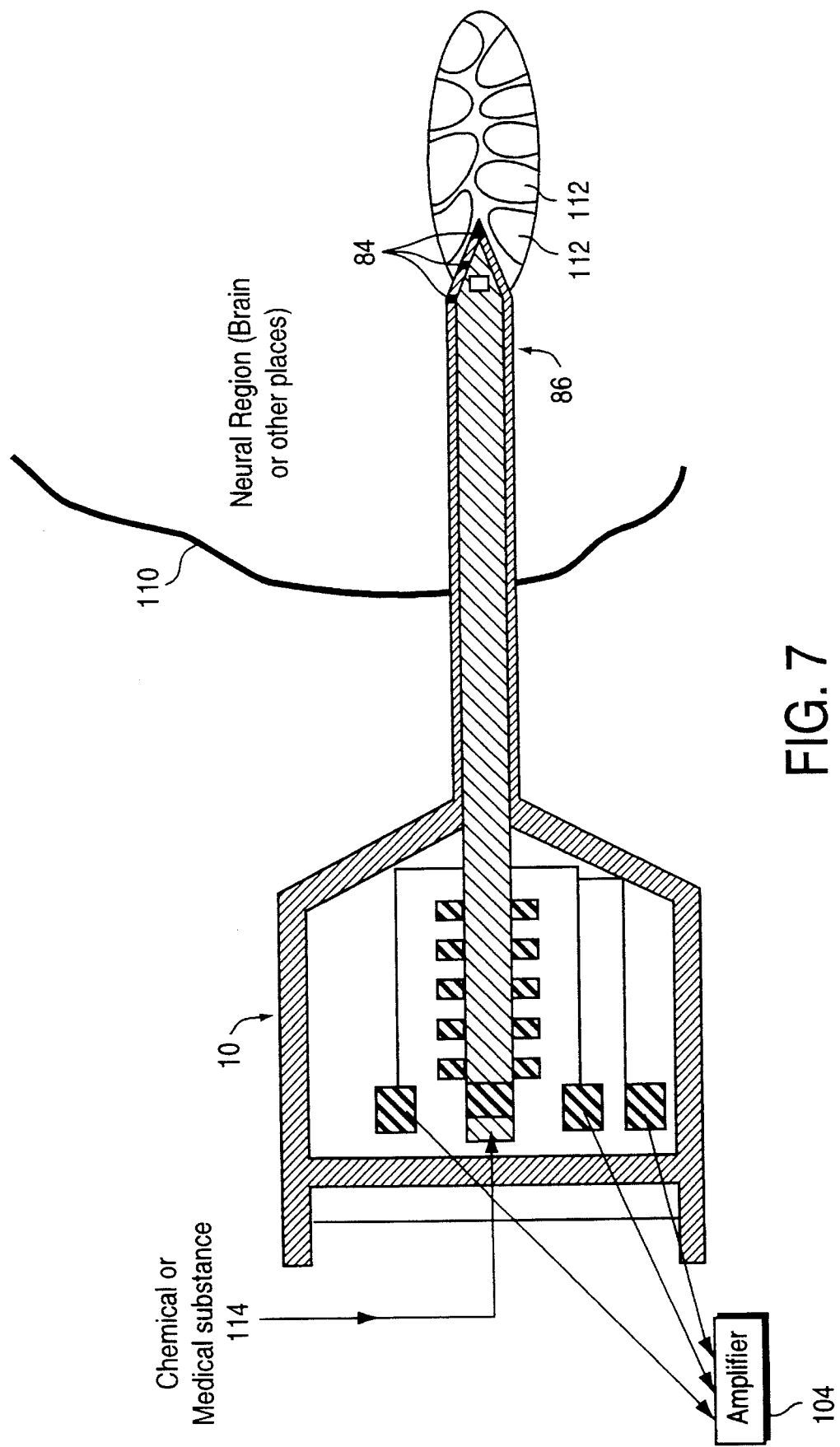
FIG. 7 is a schematic diagram including a detailed portion showing the microneedle penetrating tissue in another application of microneedle use.

Another application of the microneedle is shown in FIG. 7, in which the microneedle is used for recording neural signals. Specifically, microneedle 10 is inserted into neural tissue 110 such that tip region 86 is between adjacent cells 112. As a chemical substance 114 is delivered to neural tissue 110, recording sites or electrodes 84 on tip 86 detect the neural response to substance 114. The recording sites passively detect a signal which is relayed to an amplifier 104, as discussed above. Since microneedle 10 is so small, the damage caused by penetrating brain tissue is reduced. Additionally, recording or electrode sites 84 provide the ability to obtain real-time neural measurements. Alternatively, recording sites 84 may be used to measure neural activities or to apply an electric field, current, charge or voltage to the tissue. Processing electronics may be located separate from the interface region, as desired. Additionally, an active device may be positioned at the tip of the microneedle to process a detected signal.

Figure 8A:
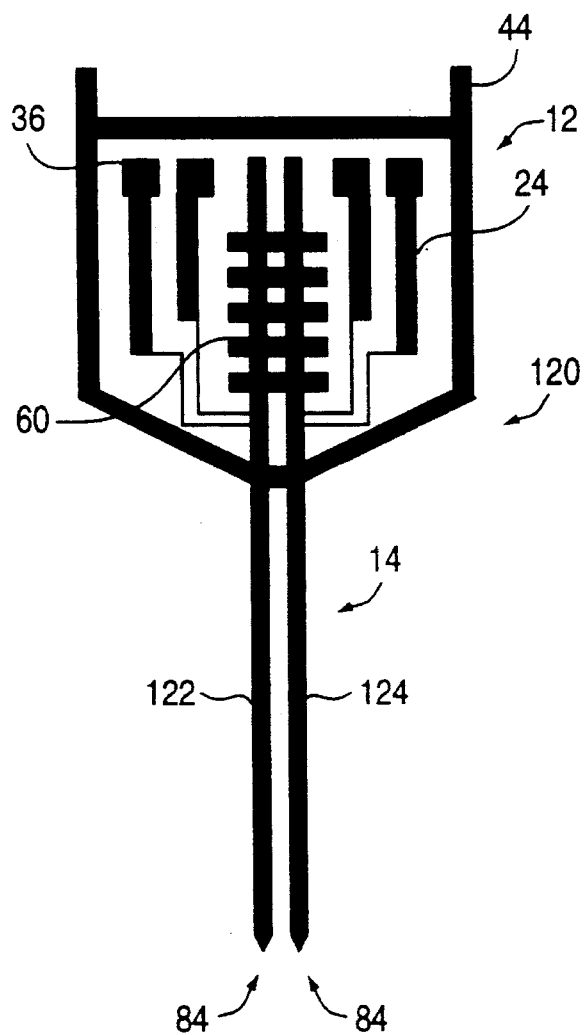
FIGS. 8A and 8B show alternative embodiments of the microneedle.
Figure 8B:
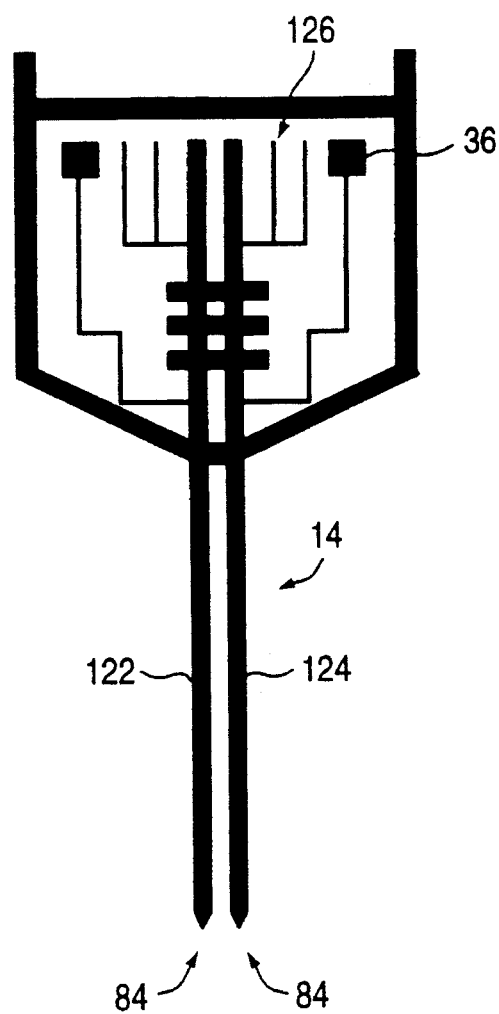

FIGS. 8A and 8B show alternative embodiments of a microneedle 120. The microneedle may include two or more microchannels 122 and 124 so that two different fluids may be delivered via the shaft 14. Microchannels 122 and 124 are formed on separate portions of a substrate, and there is no substrate between them. Additionally, electrodes 84 may be fabricated at the end of each channel to detect tissue response to chemical delivery. Electronics 24 may be fabricated as necessary depending upon the number of channels, electrodes, etc. As shown in FIG. 8B, shank end 12 may also include a network of channels 126 for distributing a fluid for analysis. Alternatively, if a number of fluids must be mixed just before delivery, it is possible to have them mix in channels 122 and 124.

In summary, an apparatus and method for a IC-processed microneedle have been described. Microneedle 10 has onboard resistive heaters 60 for bubble-pumping elements, fluid ports 18 for liquid/gas transport, and IC-interface region that can be used for future on-chip circuitry and microfluidic components. The process for producing the needles is advantageous because the needles are surrounded by regions of silicon having full wafer thickness. This feature simplifies post-processing, handling, and lead attachment which can be accomplished prior to freeing the microneedle by breaking support beams. The mask fabrication process is compatible with IC processes. The microneedles are sufficiently sturdy to penetrate tissue without being damaged and without significant pain to the patient. Since the microneedle may be batch fabricated, the resulting microneedle is relatively inexpensive to produce as compared to a macroneedle. The size of the shaft diameter may be readily controlled using known semiconductor fabrication techniques.

The present invention has been described in terms of a preferred embodiment. The invention, however, is not limited to the embodiment depicted and described. Rather, the scope of the invention is defined by the appended claims.

What is claimed is:

1. A microstructure, comprising:

a substrate having an interface region and an elongated region extending from said interface region; and a shell connected with said substrate along said elongated region and at least a portion of said interface region;

wherein said substrate and shell define a shaft having an enclosed channel.

2. The microstructure of claim 1 further including:

a plurality of shells connected with said substrate along said elongated region and at least a portion of said interface region;

wherein said substrate and shells define a plurality of enclosed channels.

3. The microstructure of claim 1 wherein said channel has a width of between about 30 and 60 micrometers, and a height of about 9 micrometers or less.

4. The microstructure of claim 1 wherein:

said shaft includes a first end at said interface region, a second end distal from said first end, and at least two ports for permitting movement of a fluid therethrough.

5. The microstructure of claim 4 further including:

heating means at said first end of said shaft for heating a liquid within said shaft, whereby said liquid forms a bubble and moves within said shaft.

6. The microstructure of claim 5 wherein said heating means comprises a polysilicon resistor.

7. The microstructure of claim 4 further including:

detecting means on said elongated portion for monitoring electrical activity generated by biological tissue in which said microstructure is inserted.

8. The microstructure of claim 7 wherein said detecting means is located at said second end of said shaft.

9. The microstructure of claim 7 wherein said detecting means includes:

a polysilicon resistor.

10. The microstructure of claim 8 wherein said distal end is of dimensions suitable to be inserted between adjacent cells of biological tissue.

11. The microstructure of claim 10 further including a chemical contained in said channel, wherein the chemical is delivered to biological tissue through said channel, and said detector means records the response of the biological tissue to the chemical, providing a real-time measurement of the biological tissue, when the distal end is inserted into biological tissue.

12. The microstructure of claim 8 further including a detector electrode extending from said detector means to said interface region.

13. The microstructure of claim 12 wherein said detector electrode extends through said channel.

14. The microstructure of claim 4 further including fluid movement means for moving a fluid along said shaft.

15. The microstructure of claim 14 wherein said fluid movement means includes:

a plurality of resistors fabricated proximate each other, wherein when said resistors are heated in sequence, a vapor bubble produced is moved sequentially along said resistors.

16. The microstructure of claim 15 wherein said plurality of resistors are positioned in a line.

17. The microstructure of claim 4 wherein a first of said at least two ports is located at said first end of said shaft and a second of said at least two ports is located at said second end of said shaft.

18. The microstructure of claim 4 further including electronic components fabricated on said interface region.

19. The microstructure of claim 18 wherein said components are CMOS devices.

20. The microstructure of claim 4 further including a plurality of end channels converging at said first end and communicating with said enclosed channel.

21. The microstructure of claim 4 wherein its elements are formed by integrated-circuit microfabrication methods.

22. The microstructure of claim 4 wherein said interface region has an area of about 2 to 3 millimeters square, said elongated region has a length of between about 1 to 6 millimeters, and said shaft has a height of about 70 micrometers.

23. The microstructure of claim 4 further comprising a blood analysis amplifier and A/D converter positioned on said interface region, said A/D converter connected to said blood analysis amplifier, wherein blood is draw into said channel and communicated to said blood analysis amplifier, and real-time blood information is transmitted to an external source via the A/D converter when said distal end is inserted into a blood vessel.

24. An microneedle, comprising:

an interface region having an area of 2 to 3 millimeters square; and an elongated hollow shaft connected to and extending from said interface region for permitting movement of a fluid therethrough, said shaft having a length of between about 1 and 6 millimeters, said shaft having at a distal end width of about 50 micrometers or less and a height of about 9 micrometers or less.

25. The microneedle of claim 24 further including at least one resistor located within said shaft for heating a fluid to form a bubble that moves along said shaft.

26. A microstructure fabricated by a process comprising the steps of:

providing a substrate for forming an interface region and an elongated portion extending away from said interface region, said substrate including a frontside and a backside;

forming a patterned, non-planar etchable structure on the frontside of said elongated portion;

depositing an unetchable membrane layer atop said etchable structure;

opening at least one etching hole in said membrane layer; and etching said etchable structure by placing an etchant into said etching hole, said etchable structure being etched to a predetermined extent to form a cavity underneath said membrane layer, thereby producing a shaft formed from said membrane layer and said elongated portion of said substrate.

* * * * *